United States Patent [19]

Ashenfelter et al.

[11] 4,188,533
[45] Feb. 12, 1980

[54] WINDOW TRANSMITTANCE TESTER

[75] Inventors: Ernest W. Ashenfelter, Wichita; Fred M. Dickey, Derby; Jerry R. White, Wichita, all of Kans.

[73] Assignee: The Boeing Company, Wichita, Kans.

[21] Appl. No.: 867,794

[22] Filed: Jan. 9, 1978

[51] Int. Cl.² ............................................. G01J 1/00
[52] U.S. Cl. ...................................... 250/338; 250/341
[58] Field of Search ............... 250/338, 339, 340, 341, 250/351, 353, 358 R; 356/173, 189, 201, 205

[56] References Cited

U.S. PATENT DOCUMENTS 3,770,355 11/1973 Anthon ............................ 250/341 X Primary Examiner—Davis L. Willis
Attorney, Agent, or Firm—Edwin H. Crabtree

[57] ABSTRACT

An infrared window transmittance tester utilized for measuring the transmission of windows used in military and commercial infrared imaging systems.

10 Claims, 5 Drawing Figures

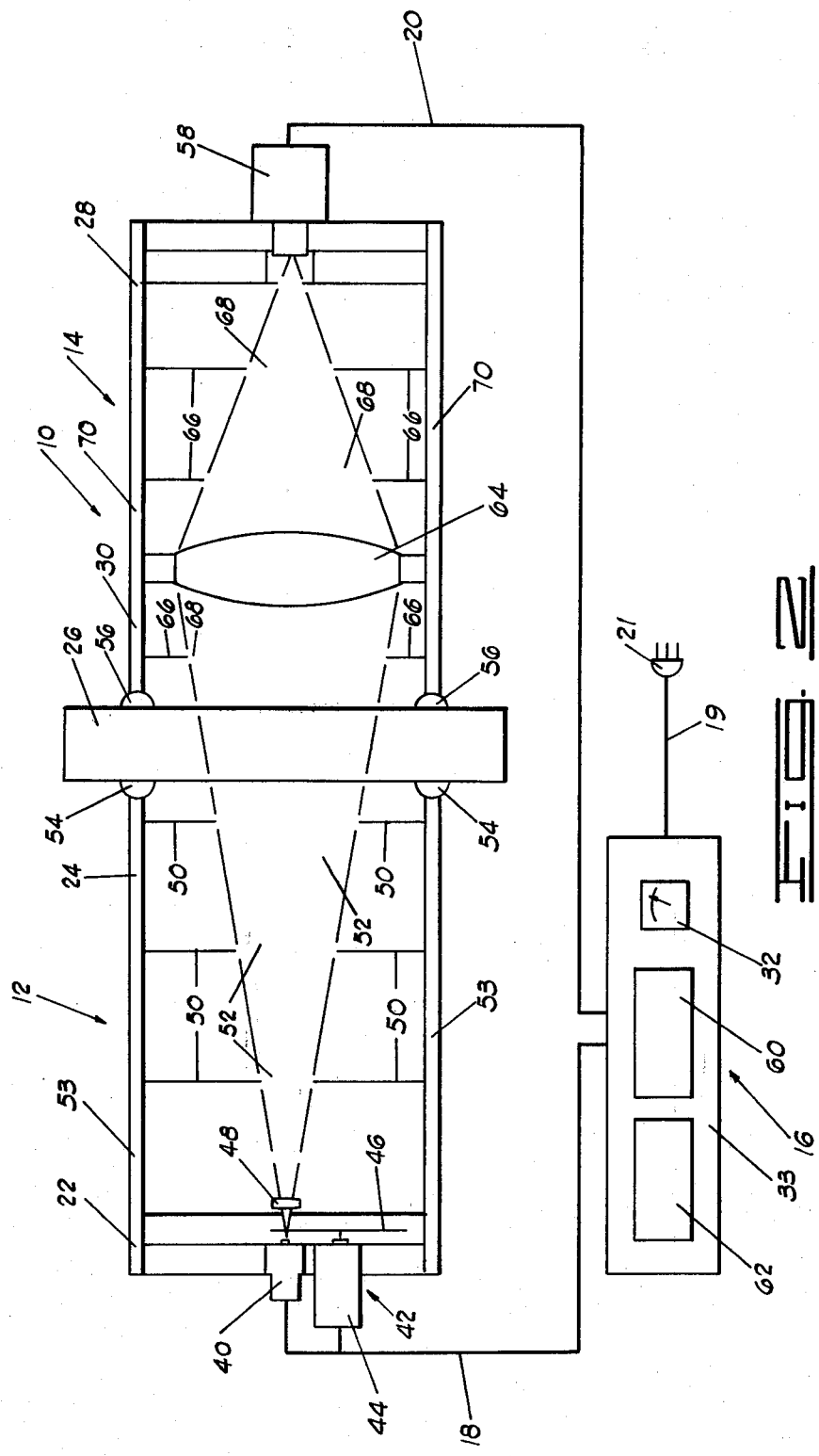

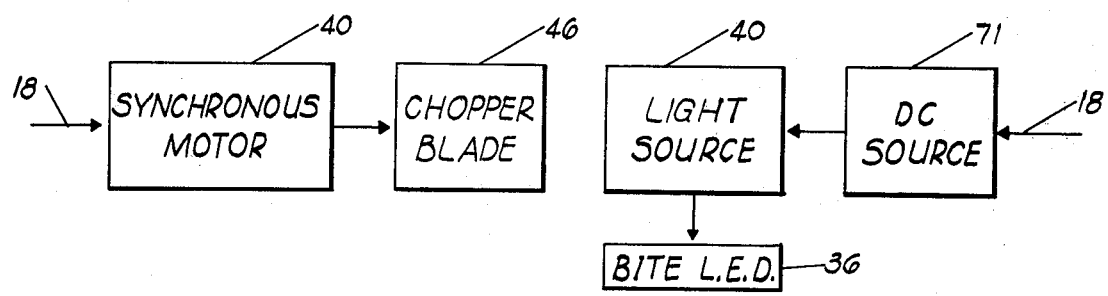
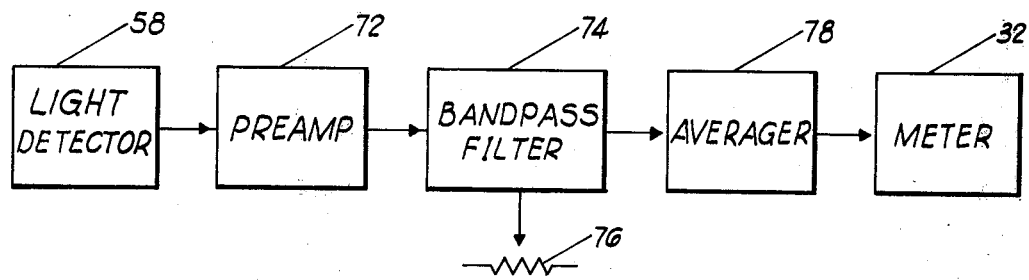
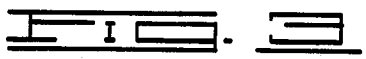
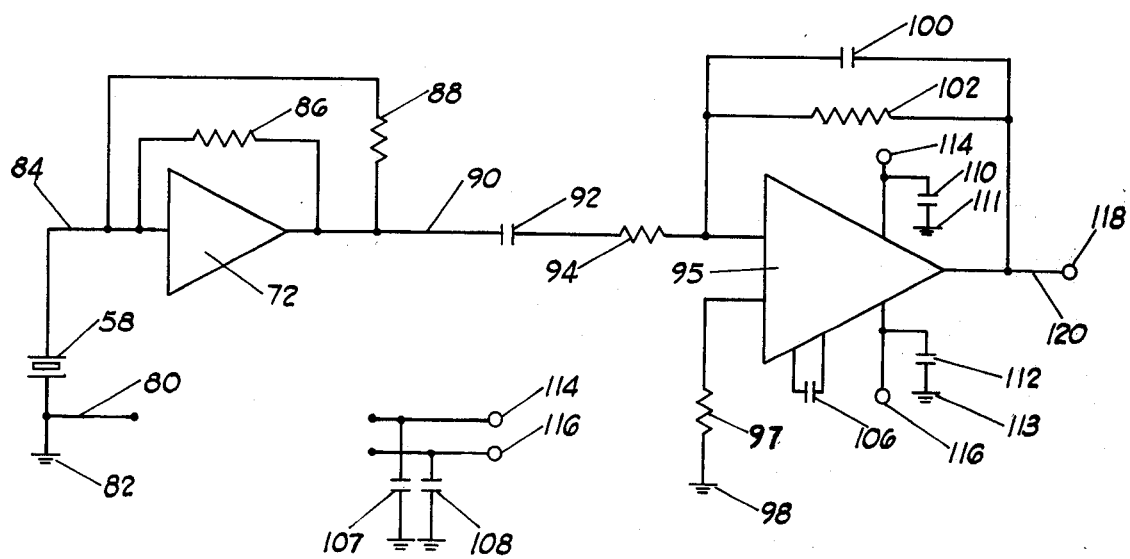
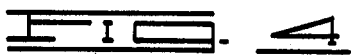

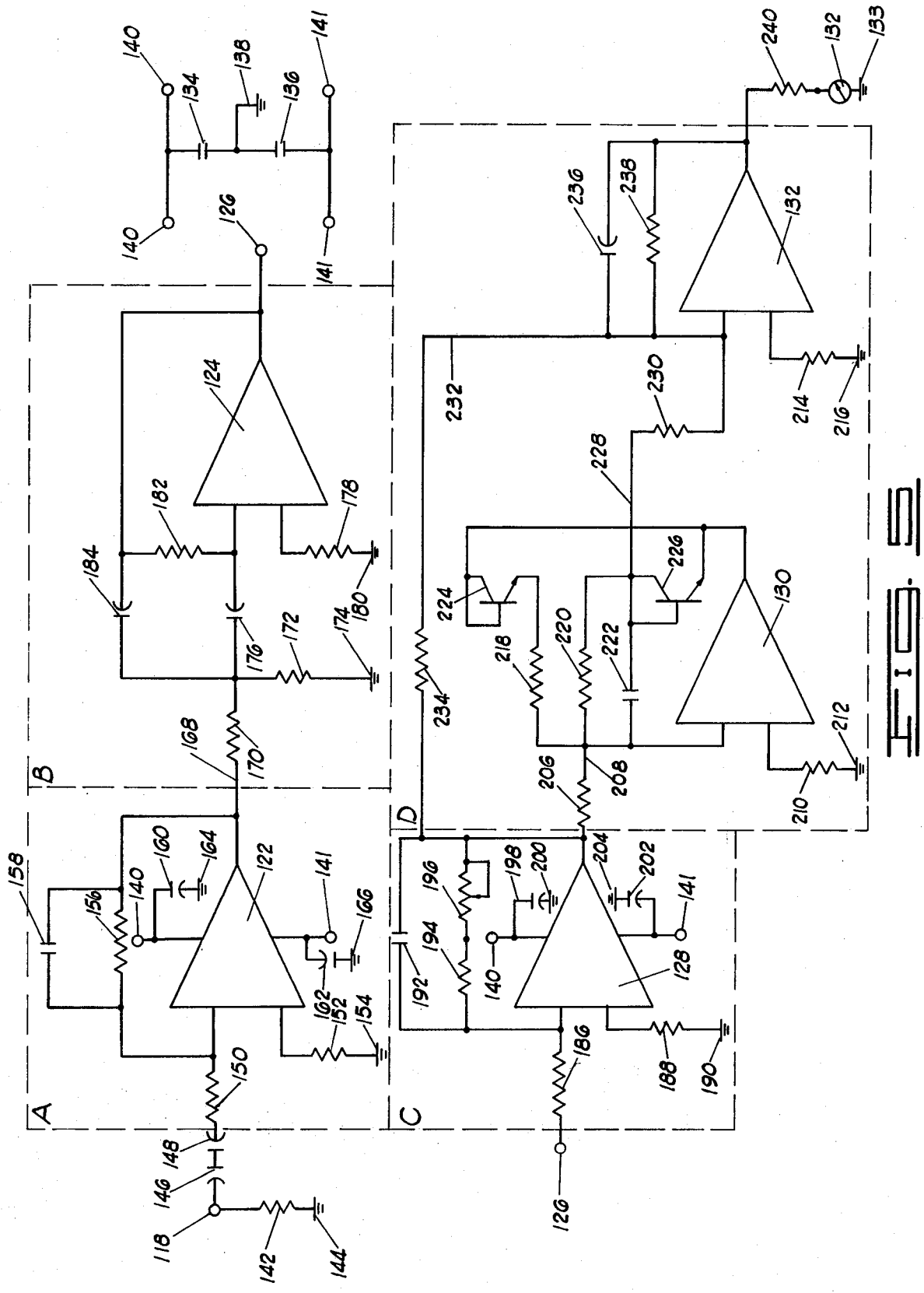

WINDOW TRANSMITTANCE TESTER

BACKGROUND OF THE INVENTION

This invention relates generally to the testing of electromagnetic radiation transmission and more particularly, but not by way of limitation, to a window transmittance tester for testing the amount of infrared radiation transmitted through a window.

Infrared imaging systems are utilized by the military for various mission functions. In addition, there are various infrared imaging systems available for commercial applications. For military aircraft, special windows are necessary to provide the required optical and mechanical performance. The special characteristics and sizes of these windows make them generally very expensive. The surfces and therefore the optical characteristics of the windows are affected by weather and particle erosion and electro-chemical reactions of the window coatings with air pollutants. Therefore, a periodic check of the window transmission is an important consideration to insure satisfactory performance of the windows and timely replacement if and when required.

At the present time, the only method of determining satisfactory window performance is through the use of large and difficult-to-use test equipment in laboratories. There is no satisfactory field equipment for checking window transmission prior to the subject invention.

SUMMARY OF THE INVENTION

The subject invention provides a portable, lightweight, small, and easy-to-operate window transmittance tester for checking infrared transmission of an infrared window.

The tester eliminates the indescriminate replacement of expensive windows used with infrared systems which can occur without a satisfactory method of measuring window performance. The invention eliminates the use of large, difficult-to-use, and costly laboratory equipment which typically require windowpane disassembly. Also, the tester principle may be used for testing other types of optical elements.

The window transmittance tester for testing the infrared radiation transmitted through a window includes a radiation source head and a detector head. Each head has a closed first end portion and an open second end portion. The open second end portions are disposed on opposite sides of the window to be tested. A radiation source connected to an electrical power supply is mounted in the closed first end portion of the light source head. The source direct radiation outwardly through the head and through the test window. The detector head includes a radiation detector mounted in the closed first end portion of the detector head for receiving the radiation passed through the test window and converting it into an electrical signal. The detector is electrically connected to a meter mounted in a meter housing. The meter receiving the electrical signal from the detector provides a reading of the radiation transmitted through the test window.

The advantages and objects of the invention will become evident from the following detailed description when read in conjunction with the accompanying drawings which illustrate the preferred embodiments of the invention.

BRIEF DESCRIPTION OF THE DRAWINGS

FIG. 2 is a side sectional view illustrating the components mounted in the radiation source head and detector head.

FIG. 3 illustrates the electronics circuitry for the radiation source head and detector head.

FIG. 4 is an electrical diagram of the electronics used in the detector preamplifier and postamplifier.

FIG. 5 is an electrical diagram of the signal processing electronics from the detector to the meter in the electronics housing.

DETAILED DESCRIPTION OF THE DRAWINGS

Figure 1:
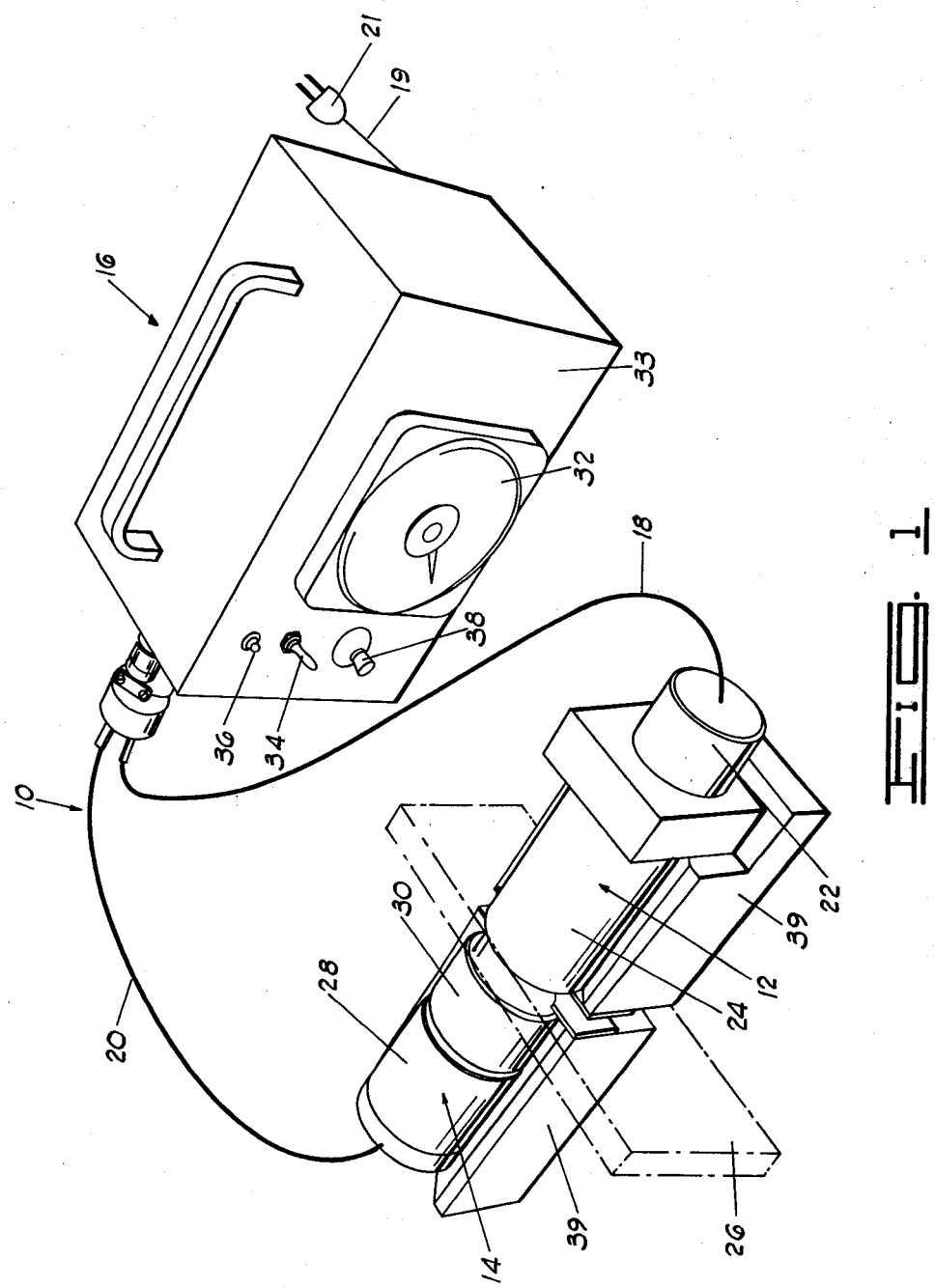
In FIG. 1, a perspective view of the window transmittance tester is illustrated.

In FIG. 1, the window transmittance tester is designated by general reference numeral 10. The tester 10 includes a radiation source head 12, a detector head 14, and an electronics housing 16. The radiation source head 12 is electrically connected to the electronics housing 16 by electric lead 18. The detector head 14 is electronically connected to the electronics housing 16 by electric lead 20. The electronics housing 16 is electrically connected to a power source by electric lead 19 and plug 21. The power source may be standard 120 volt AC power.

The radiation source head 12 includes a first end portion 22 and an open second end portion 24. The open second end portion 24 is disposed adjacent a test window 26. Disposed on the opposite side of the test window 26 is the radiation detector head 14 having a first end portion 28 and an open second end portion 30 adjacent the test window 26 and in alignment with the second end portion of the radiation source head 12. The radiation source head 12 generates radiation which passes through the test window 26 where it is received by the radiation detector head 14. The radiation received is converted to an electrical signal which is transmitted to the electronics housing 16 and read by a meter 32 which is mounted on the front 33 of the electronics housing 16. Also mounted in the front 33 of the electronics housing 16 is a power "on" and "off" switch for turning the electrical power on for the tester 10. Also, a light emitting diode 36 is electrically connected in the tester 10 for indicating that the radiation source is on and being transmitted through the test window 26.

Prior to testing the test window 26, the test window 26 is removed and the power switch 34 is turned "on". The meter 32 is adjusted for reading 100 percent by a gain knob 38. When the meter 32 has been calibrated, the radiation source head 12 and detector head 14 are placed on either side of the window 26 for determining the amount of infrared transmission therethrough. The heads 12 and 14 may be placed on head stands 39 for preventing any movement during the testing of the window 26.

In FIG. 2, a side cross-sectional view of the radiation source head 12 and detector head 14 are illustrated with the test window 26 therebetween.

A radiation source 40 is mounted in the first end portion 22 of the head 12 and directs radiation outwardly through the open second end portion 24. The radiation source 40 may be a current heated filament such as a glowplug having a rhodium-platinum heating element for approximating a point source of radiation. Mounted also in the first end portion 22 of the head 12 and adjacent the radiation source 40 is an electrically operated chopper 42 having a synchronous motor 44 rotating a chopper blade 46 which passes in front of the radiation source 40. The chopper 42 is a standard chopper for providing a modulated radiation source and allowing electronic separation of the background radiation from the tester radiation. Mounted in front of the chopper blade 46 and attached to the head 12 is a filter 48 for limiting the spectral range of the radiation as it is transmitted outwardly through the head 12. The optics of the filter 48 will vary depending on the spectral range desired from the radiation source 40.

Also, mounted between the filter 48 and the open second end portion 24 of the head 12 are a number of baffles 50 disposed in a spaced relationship to each other and having an opening 52 which increases in width from the first end portion 22 to the open second end portion 24. The openings 52 provide a light cone with the desired angular divergence.

The head 12 has a thermally conductive housing 53 having a high absorption coating for absorbing excess radiation in the head 12 and re-radiating the radiation outwardly away from the head 12.

Mounted on the edges of the open second end portion 24 are non-destructive window contacts 54 which are made of soft plastic, rubber, or the like to prevent the scratching of the coating on the test window 26. The detector head 14 also includes non-destructive window contacts 56 mounted on the edges of the open second end portion 30.

The detector head 14 includes a radiation detector 58 which is used for receiving the radiation transmitted through the test window 26 and converting the radiation to an electrical signal which is amplified by a preamplifier. The electrical signal is transferred to the electrodes housing 16 by the electrical lead 20. In the electronics housing 16 is shown a box 60 for receiving the electrical signal from lead 20. The box 60 represents the signal electronics discussed in FIG. 5 which is connected to the meter 32 for indicating the amount of radiation transmission received through the test window 26. Next to the electronics box 60 is a power supply box 62 for the distribution of the electrical power to the heads 12 and 14 and to the housing 16.

The detector head 14 further includes a collecting lens 64 mounted in the head 14 for receiving the radiation passing through the test window 26. The lens 64 includes an anti-reflection coating and is designed for optimum transmission of the particular spectral range of interest when measuring the infrared transmission.

A number of baffles 66 in a spaced relationship to each other are mounted in the head 14 and include openings 68 for providing a light cone with the desired cross-sectional area at each location for conveying the radiation to the detector 58.

The detector head 14 includes a thermally conductive housing 70 having a high absorption coating similar to the housing 53 surrounding the head 12.

In FIG. 3, an electrical flow diagram of the power input to the radiation source head 12 and to the detector head 14 is illustrated. AC power is supplied through electrical lead 18 to the synchronized motor 40 which in turn drives the chopper blade 46. The power supply from lead 18 is also converted to a DC power source 71 for driving the radiation source 40. The radiation source 40 is electrically connected to the light-emitting diode 36 which is mounted in the front 33 of the electronics housing 16.

From the radiation detector 58, the radiation received is converted to an electrical signal which is amplified by a preamplifier 72. From the preamplifier 72, the signal is conducted to an electrical bandpass filter 74. The bandpass filter 74 is connected to a gain potentiometer 76 which is attached to the gain knob 38 for calibrating the meter 32 prior to testing the test window 26. From the bandpass filter 74, the electrical signal goes to an average 78 which employs a rectifier for averaging the oscillating signal prior to being read on the meter 32.

In FIG. 4, the electronic circuitry of the radiation detector 58 preamplifier 72, and by-pass filter 74 is illustrated.

From left to right, the radiation detector 58 is attached to the head 14 by lead 80 having a ground 82. The detector 58 transduces the radiation received into electrical signal which is conducted by lead 84 to amplifier 72.

The amplifier 72 includes an internal gain resistor 86 and an external gain resistor 88 which are connected in parallel to the input and output of the amplifier 72. From the output of the amplifier 72, a lead 90 is connected to an AC coupling capacitor 92. From the capacitor 92, the lead 90 is connected to an amplifier input resistor 94, which is connected to a postamplifier 95 which acts as the bandpass filter 74. The amplifier 95 is attached to the bias resistor 97 which in turn is attached to a ground 98. The postamplifier 95 includes a capacitor 100 for low pass filtering and an amplifier feedback resistor 102 which are parallel to each other and connected to the input and output of the amplifier 95. The amplifier 95 also includes an external compensation capacitor 106. The amplifier 95 is powered by the power supply with the addition of filter capacitors 107 and 108 which are connected to power supply by-pass capacitors 110 and 112 at terminals 114 and 116. The capacitors 110 and 112 include grounds 111 and 113. The power supply by-pass capacitors 110 and 112 provide AC component filtering of the plus and minus DC voltage. The output of the amplifier 95 is conducted to a terminal 118 by lead 120. The terminal 118 is connected to the input buffer amplifier 122 shown in FIG. 5.

In FIG. 5, the electronic circuitry for driving the signal processing electronics to the meter 32 is shown.

The signal processing electronics for processing of the electrical signal to the meter 32 includes the input buffer amplifier 122 having a circuit network designated as reference A and encircled in dotted lines. The output signal from network A is processed by a second order multiple feedback bandpass filter network, designated by reference B shown in dotted lines, and having an operational amplifier 124. The output from the amplifier 124 goes to a terminal 126 which is then processed by an adjustable gain amplifier network, designated by reference C shown in dotted lines, and having an operational amplifier 128. From the output of the amplifier 128, the signal is finally processed by an absolute value and averaging network D, surrounded in dotted lines, and having a pair of operational amplifiers 130 and 132. From the network D, the signal is received by the meter 32 having a ground 133.

The above-mentioned amplifiers are supplied by plus and minus DC voltage filtered by power supply filter capacitors 134 and 136. The capacitors 134 and 136 include a ground 138 and terminals 140 and 141 which are wired to the amplifiers.

The input terminal 118 includes a line terminating resistor 142 having a ground 144. The input is fed through a pair of AC coupling capacitors 146 and 148 and through an input resistor 150. Attached to the input of the amplifier 122 is an input current bias resistor 152 having a ground 154. The input and output of the amplifier 122 include an amplifier feedback resistor 156 and a capacitor 158 for low-pass filtering wired in parallel. The amplifier 122 further includes power supply bypass capacitors 160 and 162 having grounds 164 and 166. The capacitors 160 and 162 are attached to the plus voltage terminal 140 and minus voltage terminal 141.

From the output of the amplifier 122, the signal is fed through lead 168 through an amplifier input resistor 170. The lead 168 is connected to an additional amplifier input resistor 172 having a ground 174. The input signal is fed through an amplifier input capacitor 176. The input of the amplifier 124 includes an input current bias resistor 178 having a ground 180. An amplifier feedback resistor 182 is wired to an amplifier feedback capacitor 184 which is connected to the input and output of the amplifier 124. The output of the amplifier 124 is connected to terminal 126 and then fed through an input resistor 186 of the adjustable gain amplifier network C.

The input of the amplifier 128 includes an input current bias resistor 188 having a ground 190. A capacitor 192 for low-pass filtering, a fixed value amplifier feedback resistor 194, and a gain adjust amplifier feedback resistor 196 are connected to the input and output of the amplifier 128. The resistor 196 is used for adjusting the gain of the amplifier 128. The resistors 194 and 196 are in parallel with the capacitor 192. The amplifier 128 further including power supply by-pass capacitor 198 having a ground 200 attached to the plus voltage terminal 140 and a power supply by-pass capacitor 202 having a ground 204 and attached to the minus voltage terminal 141. The output from the amplifier 128 is fed through input resistor 206 and then through lead 208 to the input of the amplifiers 130 and 132. The amplifiers 130 and 132 include input current bias resistors 210 having a ground 212 and input current bias resistor 214 having a ground 216.

Connected to lead 208 and in parallel to each other is an amplifier feedback resistor 218, an amplifier feedback resistor 220, and a low-pass filtering capacitor 222. The resistor 218 is attached to the output of a transistor 224 which is connected to the output of the amplifier 130. A second transistor 226 is also connected to the output of the amplifier 130 and is connected to the resistor 220 and capacitor 222. The output of the amplifier 130 is fed through lead 228 and through input resistor 230 to the amplifier 132. A second lead 232 connected to the output of the amplifier 128 is fed through an input resistor 234 which is connected to an averaging capacitor 236 and an amplifier feedback resistor 238 which are mounted in parallel to the input and output of the second operational amplifier 132. The output of the amplifier 132 is then fed through a current limiting resistor 240. The signal is then read on the meter 32 for indicating electrically the amount of radiation transmission through the test window 26.

Changes may be made in the construction and arrangement of the parts or elements of the embodiment as disclosed herein without departing from the spirit or scope of the invention as defined in the following claims.

We claim:

1. A window transmittance tester for testing the infrared radiation transmission through a test window, the tester comprising:
   a hand held self-contained portable radiation source head having a first end portion and an open second end portion, the open second end portion of the said head disposed adjacent and tangent the test window;
   a radiation source connected to an electrical power source and mounted in the first end portion of said radiation source head, said radiation source directed through said head outwardly through the open second end portion of said head and through the test window, said radiation source providing a spectral range of radiation;
   a hand held self-contained portable detector head having a first end portion and an open second end portion, the open second end portion of said detector head disposed adjacent and tangent the test window and on the opposite side of the test window from the second end portion of said radiation source head and in alignment therewith;
   a detector connected to an electrical power sorce and mounted in the first end portion of said detector head for receiving said radiation through the test window and converting said radiation to an electrical signal;
   an optical lens mounted in said detector head between the open second end portion and said detector for receiving said radiation from the test window and optically conveying said radiation to said detector; and
   an electrically operated meter mounted in an electronics housing and connected to said detector for receiving the electrical signal therefrom and measuring the radiation transmitted through the test window.

2. The tester as described in claim 1 further including a chopper connected to an electrical power source and mounted in the first end portion of said radiation source head, said chopper having a chopper blade disposed between said radiation source and the second end portion of said radiation source head for mechanically separating the radiation from said radiation source from background radiation in said radiation source head and providing a modulated radiation transmission through the test window.

3. The tester as described in claim 1 further including a number of baffles mounted in a spaced relationship to each other between the first end portion and the open second end portion of said radiation source head, said baffles having an opening through the center thereof, the opening in said baffles defining a cone having a desired angular divergence.

4. The tester as described in claim 1 further including a number of baffles mounted in a spaced relationship to each other between the first end portion and the open second end portion of said detector head, said baffles having an opening through the center thereof, the opening in said baffles defining a cone having a desired cross-sectional area.

5. The tester as described in claim 1 further including a filter mounted in the first end portion of said radiation source head and disposed between said radiation source and the second end portion of said head for optically limiting the spectral range of the source radiation from said source.

6. The tester as described in claim 1 wherein said radiation source is an electrical current heated filament.

7. A window transmittance tester for testing the infrared radiation transmission through a test window, the tester comprising:
- a hand held self-contained portable radiation source head having a first end portion and an open second end portion, the open second end portion of said head disposed adjacent and tangent the test window;
- a radiation source connected to an electrical power source and mounted in the first end portion of said radiation source head, said radiation source directed through said head outwardly through the open second end portion of said head and through the test window, said radiation source providing a spectral range of infrared radiation;
- a chopper connected to an electrical power source and mounted in the first end portion of said radiation source head, said chopper having a chopper blade disposed between said radiation source and the open second end portion of said radiation source head for mechanically modulating the infrared radiation from said radiation source to allow for separation of the source radiation from the background radiation in the electronic processing by the tester;
- a number of baffles mounted in a spaced relationship to each other between the first end portion and the open second end portion of said radiation source head, said baffles having an opening through the center thereof, the opening of said baffles defining a cone having a desired cross-sectional area;
- a filter mounted in the first end portion of said radiation source head disposed between said radiation source and the second end portion of said head for optically limiting the spectral range of the infrared radiation of said source;
- a hand held self-contained portable detector head having a first end portion and an open second end portion, the open second end portion of said detector head disposed adjacent and tangent the test window and on the opposite side of the second end portion of said radiation source head and in alignment therewith;
- a detector connected to an electrical power source and mounted in the first end portion of said detector head for receiving radiation from said source through the test window and converting said radiation to an electrical signal;
- an optical lens mounted in the second end portion of said detector head for receiving said radiation through the test window and optically conveying said radiation to said detector;
- a number of baffles mounted in said detector head and in a spaced relationship to each other, said baffles having an opening through the center thereof, the opening of said baffles defining a cone having a desired cross-sectional area; and
- an electrically operated meter mounted in an electronics housing and connected to said detector for receiving the electrical signal from said detector and measuring the radiation transmission through the test window.

8. The tester as described in claim 7 further including non-destructive window contacts mounted on the ends of the open second end portions of said radiation source head and said detector head for contacting the surface of the test window under test and preventing the damage thereof.

9. The tester as described in claim 7 wherein said radiation source head and said detector head include thermally conductive housings having high absorption coatings for absorbing stray background radiation.

10. The tester as described in claim 7 wherein said optical lens includes an anti-reflection coating and is designed for optimum transmission in a specific spectral range of interest.

* * * * *